US00PP20760P2

(12) United States Plant Patent
Giesen

(10) Patent No.: US PP20,760 P2
(45) Date of Patent: Feb. 16, 2010

(54) *LOBELIA* PLANT NAMED 'TECH HEPLIB'

(50) Latin Name: *Lobelia erinus*
Varietal Denomination: Tech Heplib

(75) Inventor: Eric Giesen, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/284,781

(22) Filed: Sep. 25, 2008

(51) Int. Cl.
*A01H 5/00* (2006.01)

(52) U.S. Cl. ..... Plt./451

(58) Field of Classification Search ..... Plt./451
See application file for complete search history.

*Primary Examiner*—June Hwu
(74) *Attorney, Agent, or Firm*—S. Matthew Edwards

(57) ABSTRACT

A new *Lobelia* plant named 'Tech Heplib,' particularly distinguished by light blue and white flowers, medium green foliage, freely branching, bushy, mounding plant habit, relatively upright stems, hardly cascading, and medium to tall plant in size.

1 Drawing Sheet

Latin name of the genus and species of the plant claimed: *Lobelia erinus.*

Varietal denomination: 'Tech Heplib'.

BACKGROUND OF THE NEW PLANT

The present invention comprises a new and distinct cultivar of *Lobelia*, botanically known as *Lobelia erinus* and hereinafter referred to by the cultivar name 'Tech Heplib.'

'Tech Heplib' is a product of a planned breeding program. The new cultivar originated from a hybridization made in January 2004 in Andijk, Netherlands.

The female parent was an unpatented proprietary *Lobelia* plant designated 'LOB03-113-1,' with light blue flower color. 'LOB03-113-1' has larger flowers and is more upright than 'Tech Heplib.'

The male parent of 'Tech Heplib' was an unpatented proprietary *Lobelia* plant designated 'LOB04-110-1,' having a white flower color. 'LOB04-110-1' has smaller flowers than 'Tech Heplib.'

The seeds were sown in March 2004 and 'Tech Heplib' was selected as one flowering plant within the progeny of the stated cross in July 2004 in a controlled environment in Andijk, Netherlands.

The first act of asexual reproduction of 'Tech Heplib' was accomplished when vegetative cuttings were propagated from the initial selection in the fall of 2004 in a controlled environment in Andijk, Netherlands.

Horticultural examination of plants grown from cuttings of the plant initiated in the spring of 2005 in Andijk, Netherlands, and in Hillscheid, Germany, and continuing thereafter, has demonstrated that the combination of characteristics as herein disclosed for 'Tech Heplib' are firmly fixed and are retained through successive generations of asexual reproduction.

'Tech Heplib' has not been observed under all possible environmental conditions. The phenotype may vary significantly with variations in environment such as temperature, light intensity and day length.

A Plant Breeders' Right for this cultivar was applied for with the European Union on Sep. 13, 2007. 'Tech Heplib' has not been made publicly available more than one year prior to the filing of this application.

DESCRIPTION OF THE DRAWINGS

This new *Lobelia* plant is illustrated by the accompanying photograph which shows blooms, buds, and foliage of the plant in full color. The colors shown are as true as can be reasonably obtained by conventional photographic procedures.

Figure 1:
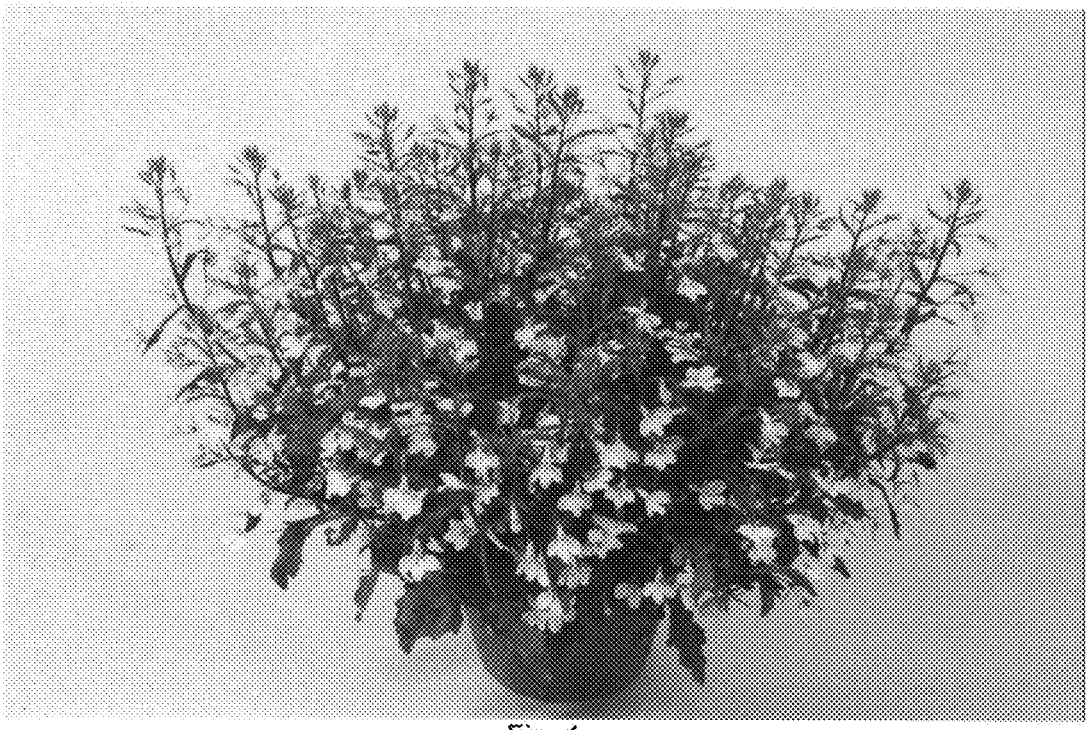
FIG. 1 shows a 17 week old potted plant with flowers, buds and foliage.
Figure 2:
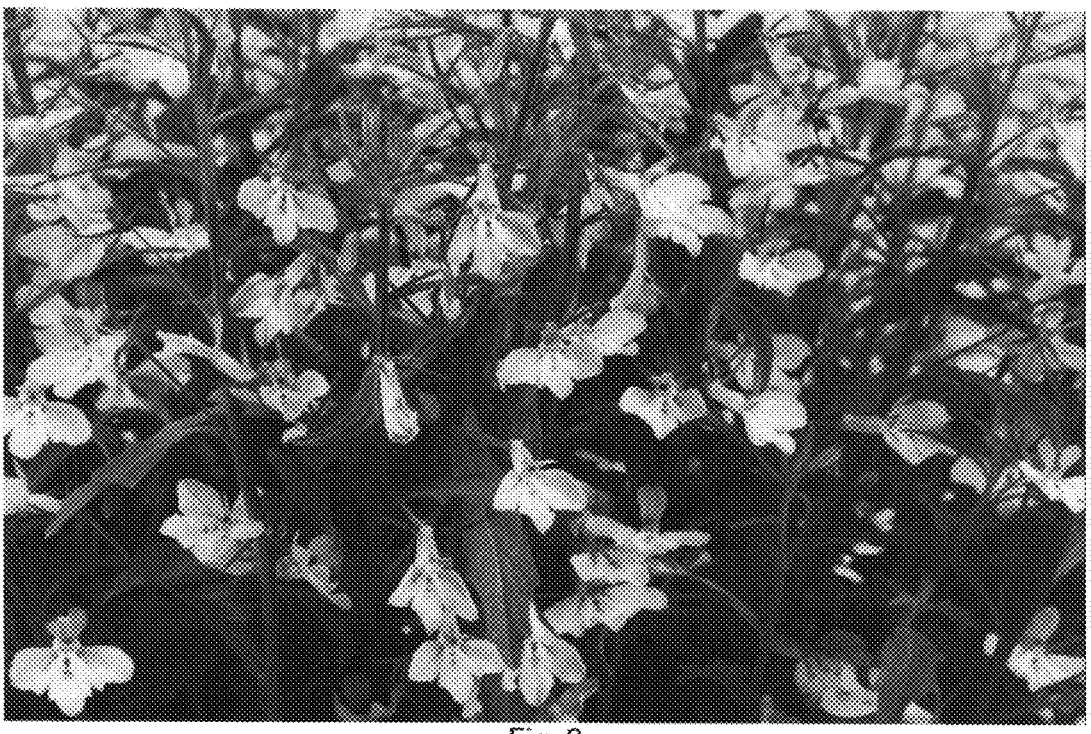
FIG. 2 is a closer view of shoots tips and flowers.

Both photographs were taken in mid May 2007.

DETAILED BOTANICAL DESCRIPTION

The measurements were taken in Hillscheid, Germany, mainly on May 5, 2007, using 15 week old plants that were growing in 12 cm pots in a greenhouse under relatively cool conditions. Culture of these plants had started in late January 2007 with planting of rooted cuttings that had been pinched once.

Color chart used: The Royal Horticultural Society Colour Chart (R.H.S.), 2001.

BRIEF SUMMARY OF INVENTION

The following observations, measurements, and comparisons describe plants grown indoors and outdoors in Andijk, Netherlands, and in Hillscheid, Germany. The following traits have been repeatedly observed and are determined to be basic characteristics of the new variety. The combination of these characteristics distinguishes this *Lobelia* as a new and distinct variety:

1. Light blue and white flowers
2. Medium green foliage
3. Well-branched and bushy, moderately compact plant habit
4. Relatively tall, mounding habit and vigorous growth
5. Semi-upright directed stems, hardly trailing

COMPARISON WITH COMMERCIAL CULTIVARS

'Tech Heplib' differs from the commercial cultivar 'Laguna Mounding Denim' (registered 'Lobden,' U.S. patent application Ser. No. 12/008,910, now abandoned) in that 'Tech Heplib' has a lighter blue flower color, grey foliage, thicker and longer stems, and with foliage surface covered with pubescences, in contrast to the glabrous or nearly glabrous leaves of 'Laguna Mounding Denim.'

'Tech Heplib' differs from the commercial cultivar 'Hot Whitespot,' registered 'Weslospot,' U.S. Plant Pat. No. 15,835, in that, with the flowers of 'Tech Heplib,' there is a less strong contrast between the blue and white color, and the plant habit of 'Tech Heplib' is smaller than that of 'Weslospot.'

Plant:

*Growth and habit.*—Vigorous growth, bushy, freely branching with medium internodes.

*Form.*—Mounding with semi-upright stems, hardly trailing.

*Height above soil.*—Approximately 20 cm.

*Plant diameter.*—35–40 cm.

*Plant spread.*—20–25 cm (from the base of the main stem to the tips of the branches).

*Spread at the end of the summer.*—55–60 cm.

*Number of branches.*—45.

*Time to produce a finished flowering plant.*—About 10–12 weeks for a 12 cm pot.

*Outdoor plant performance.*—Used in patio containers, in hanging baskets or in mixed container plantings.

*Time to initiate and develop roots.*—Approximately 24 days at 20–24° C.

*Root description.*—Fibrous and freely branching.

Stem:

*Characteristics.*—Quandrangular.

*Stem length.*—30–35 cm.

*Diameter.*—2–3 mm.

*Internode length.*—0.7–2.0 cm.

*Color.*—Deep green, R.H.S. 137A, no anthocyanin.

*Texture.*—Short hair, hirtellous.

Foliage:

*Arrangement.*—Alternate.

*Shape.*—Oblanceolate or spathulate, on flowering stems relatively small, appear sessile without any distinct petiole.

*Apex.*—Acute or broadly acute.

*Base.*—Attenuate.

*Margin.*—Dentate.

*Leaf length* (*in flowering stage*).—2.5–4.0 cm.

*Leaf width.*—0.9–1.7 cm.

*Size of leaves near the base of stems or on non-flowering stems.*—4.5–6.0 cm in length, most often about 2 cm, occasionally up to 3.5 cm wide.

*Color upper surface.*—Deep green, RHS 137A.

*Color lower surface.*—RHS 137D, anthocyanin may occur and the green color will be overlain with a RHS 183B hue.

*Venation type.*—Pinnate.

*Venation color.*—RHS 146C on the lower side, indistinct on upper side.

*Texture.*—Both surfaces covered with very short hair, and especially along the leaf veins of lower surface and at the edges.

Inflorescence:

*Blooming habit.*—Continuous through the growing season from spring to the fall.

*Begin of flowering.*—About 10 weeks after planting of rooted cuttings in spring.

*Type of inflorescence.*—Single flowers at apical axils, with one flower per leaf node.

*Quantity of flowers per stem.*—About 4–6 open flowers, additionally buds.

*Lastingness of individual blooms on the plant.*—Approximately 6–8 days.

*Fragrance.*—Very weak.

Flower:

*Corolla type and shape.*—Single, zygomorphic; lower part tube shaped, with the petal lobes opening outwards; 2 small petals directed upright and 3 mainly fused petals forming the 3-lobed lower lip.

*Flower diameter, length.*—2.0–2.2 cm.

*Corolla tube length.*—1.0–1.1 cm.

*Tube width.*—0.4 cm.

*Color upper surface.*—Ranging from RHS 97B to 97C.

*Markings in the center.*—Deeper blue macules, RHS 98C.

*Color lower surface.*—Pale blue, RHS 97D, mainly, somewhat deeper blue near margins, RHS 138C.

*Color of tube.*—Upper surface of varying intensity: RHS 96D or 97B near base, upper portion may be lighter; lower surface: RHS 97A or 97D.

Petal (lobes):

*Apex.*—Upper petals: acute; lower petals rounded to weakly mucronulate.

*Base.*—Fused.

*Margin.*—Entire.

*Texture.*—Mainly glabrous, edges of upper petal ciliated.

*Upper lobes, length* (*from the corolla opening*).—6–7 mm.

*Upper lobes, width.*—2 mm.

*Lower lobe, length* (*from the corolla opening*).—10–11 mm.

*Lower lobe, width.*—6–8 mm.

Flower bud:

*Shape.*—Oblong.

*Diameter.*—0.3–0.4 cm.

*Length.*—1.0–1.3 cm.

*Color* (*at tight bud*).—RHS 97B to 97C.

Calyx:

*Form and shape.*—5 sepals in a whorl, slanting upwards.

*Sepal color.*—RHS 137A to 137B, both surfaces.

*Length.*—6–7 mm.

*Width.*—1 mm.

*Shape of sepal.*—Ligulate.

*Apex.*—Acute, pointed.

*Base.*—Fused.

*Texture.*—Covered with short hair.

Pedicels:

*Color.*—RHS 137B.

*Length.*—Approximately 2.5 cm in length.

*Diameter.*—0.1 cm.

*Texture.*—Densely pubescent.

Reproductive organs:

Stamens:

*Quantity.*—5, somewhat twisted around the style.

*Filament, color.*—Blue, RHS 96D.

*Length.*—0.8 cm.

*Diameter.*—0.1 cm.

*Anther color.*—Grey, RHS 202B.

*Pollen amount.*—Little.

*Pollen color.*—RHS 8B.

Pistil:

*Quantity per flower.*—One.

*Length.*—About 1.0 cm.

*Stigma color.*—RHS 83D.

*Style color.*—Pale green, RHS 145C.

Fruit and seed set: Has not been observed.

Disease/pest resistance: Disease resistance or susceptibility other than typical for the species has not been observed on this hybrid.

What is claimed is:

1. A new and distinct variety of *Lobelia* plant named 'Tech Heplib,' substantially as illustrated and described herein.

* * * * *